United States Patent
Etzkorn et al.

(10) Patent No.: US 10,052,492 B2
(45) Date of Patent: Aug. 21, 2018

(54) REPLACEABLE BATTERY FOR IMPLANTABLE DEVICES

(71) Applicant: Verily Life Sciences LLC, Mountain View, CA (US)

(72) Inventors: James Etzkorn, Mountain View, CA (US); Brian Otis, Saratoga, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 133 days.

(21) Appl. No.: 14/705,961

(22) Filed: May 6, 2015

(65) Prior Publication Data
US 2016/0325105 A1    Nov. 10, 2016

(51) Int. Cl.
| | | |
|---|---|---|
| *A61N 1/37* | (2006.01) | |
| *A61N 1/378* | (2006.01) | |
| *A61N 1/375* | (2006.01) | |
| *A61N 1/372* | (2006.01) | |

(52) U.S. Cl.
CPC ........... *A61N 1/3787* (2013.01); *A61N 1/375* (2013.01); *A61N 1/37211* (2013.01)

(58) Field of Classification Search
CPC ... A61N 1/37211; A61N 1/375; A61N 1/3787
See application file for complete search history.

(56) References Cited

U.S. PATENT DOCUMENTS

| | | | |
|---|---|---|---|
| 7,953,493 B2 | 5/2011 | Fowler et al. | |
| 8,550,977 B2 * | 10/2013 | Kasic, II | A61N 1/36032 |
| | | | 600/25 |
| 8,798,752 B2 | 8/2014 | Helmut | |
| 2004/0138723 A1 * | 7/2004 | Malick | H04R 25/552 |
| | | | 607/57 |
| 2006/0183965 A1 | 8/2006 | Kasic, II et al. | |

(Continued)

FOREIGN PATENT DOCUMENTS

| | | |
|---|---|---|
| WO | 2010000026 A1 | 1/2010 |
| WO | 2015023291 A1 | 2/2015 |

OTHER PUBLICATIONS

International Search Report and Written Opinion of International Application No. PCT/US2016/028183 dated Jul. 11, 2016 (dated Jul. 21, 2016).

(Continued)

*Primary Examiner* — Amanda Patton
(74) *Attorney, Agent, or Firm* — Kilpatrick Townsend & Stockton LLP (57) ABSTRACT

Systems and methods for the wireless transfer of power between two hermetically sealed devices are described herein. An example system may include a battery package and a hermetically sealed body-implantable electronic device having an electronics package. The battery package may include one or more alignment structures, configured to removably align the battery package with the electronic device, a battery, and a wireless power transceiver. At least the battery and the wireless power transceiver of the battery package may be contained within a hermetic material separate from the electronic device. Power may be wirelessly transferred between the devices by any means, including inductive coupling or capacitive coupling. In some examples, the hermetically-sealed devices may be implanted in a living body.

15 Claims, 6 Drawing Sheets

(56) References Cited

U.S. PATENT DOCUMENTS

2007/0123938 A1   5/2007   Haller et al.
2013/0296970 A1   11/2013  Van Den Heuvel et al.
2014/0128935 A1   5/2014   Kumar et al.

OTHER PUBLICATIONS

International Application No. PCT/US2016/028183, "International Preliminary Report on Patentability", dated Nov. 16, 2017, 9 pages.

\* cited by examiner

REPLACEABLE BATTERY FOR IMPLANTABLE DEVICES

BACKGROUND

Unless otherwise indicated herein, the materials described in this section are not prior art to the claims in this application and are not admitted to be prior art by inclusion in this section.

Implantable electronic devices, such as intraocular implants, cochlear implants, and pacemakers, are often expected to provide for decades of use. In some cases, this can be fulfilled by using ultra-low power electronics and a non-rechargeable battery that is integral with the device's electronics platform. The functioning lifetime of the implantable device may, however, outlast that of the non-rechargeable battery. This essentially limits the lifetime of the implantable device to that of the battery, such that the entire implantable device is replaced once the battery expires. Because implantable devices are expensive and require large incisions to implant, replacing the entire device is not desirable.

Many additional medical device applications are becoming available if a rechargeable battery may be utilized. However, while rechargeable battery technology is advancing, rechargeable batteries only last thousands of charging cycles and require replacement after only 5-10 years. Based on current technology, a rechargeable battery will not remain functional after decades of use if the battery is recharged every day in order to power the device. As such, the overall lifetime of the device is limited by that of the battery. Because the battery is typically an integral component of the implantable device, once the battery expires, the entire implantable device is typically replaced.

SUMMARY

Systems and methods for the wireless transfer of power between two hermetically-sealed and non-electrically connected devices are described herein. Each device may include a wireless transceiver configured to wirelessly transmit and/or receive power, when brought into proximity. One of the hermetically-sealed devices may serve as a wireless power source to the second hermetically-sealed device, which may be a functional electronic device, such as an implantable medical device.

Some embodiments of the present disclosure provide a device including: (1) a battery, (2) a wireless power transceiver, configured to wirelessly transfer power to an electronics package of a body-implantable electronic device, wherein both the battery and the wireless power transceiver are enclosed within a hermetic material; and (3) one or more alignment structures, configured to removably align the device with the electronics package of the body-implantable electronic device.

Further embodiments of the present disclosure provide a body-implantable system including: (1) a hermetically sealed body-implantable electronic device comprising an electronics package; and (2) a battery package, comprising: (a) one or more alignment structures, configured to removably align the battery package with the body-implantable electronic device, (b) a battery, and (c) a wireless power transceiver; wherein at least the battery and the wireless power transceiver of the battery package are contained within a hermetic material separate from the body-implantable electronic device.

Further embodiments of the present disclosure provide a method including: (1) wirelessly transferring power from a first hermetically sealed device to a second hermetically sealed device while the first hermetically sealed device and the second hermetically sealed device are implanted within a living body and the first hermetically sealed device is removably aligned with the second hermetically sealed device, wherein the first hermetically sealed device comprises: (a) one or more alignment structures, configured to removably align the first hermetically sealed device with the second hermetically sealed device, (b) a battery, and (c) a wireless power transceiver; and wherein the second hermetically sealed device comprises a wireless power transceiver.

These as well as other aspects, advantages, and alternatives, will become apparent to those of ordinary skill in the art by reading the following detailed description, with reference where appropriate to the accompanying drawings.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

A system including a battery package configured to be removably aligned with an electronics package of an implantable electronic device is provided. Both the battery package and the electronics package of the implantable device include one or more inductive coils to allow for powering of the medical device via inductive coupling. The battery package is capable of being detached from the medical device and removed from the body with a much smaller incision than what is used to install the medical device in the body. A new battery package may be re-introduced and recoupled with the implantable device, thereby extending the lifetime of the device without complete replacement.

A first hermetically sealed package containing a battery, a coil and, in some cases, a chip, can be provided. The main electronic package of the medical device can be hermetically sealed and can include sensors, circuits, and an inductive coil. Once installed, the two coils are aligned, such as by magnets or mechanical snaps, such that power is wirelessly transferred from the battery package to the main device electronics. In some examples, wireless power transfer can be in the form of inductive coupling. In other examples, power may be wirelessly transferred by capacitive coupling. The battery can be replaced by disengaging the snaps/magnetic connections and connecting a new battery module. One advantage of this system is that the hermetic seal of the electronics package is not broken by the removal and replacement of the battery, so that the implanted device and safety of the user is not compromised. Further, the battery package may be removed and replaced with a small 1 mm incision, which is a smaller incision and a simpler process than removing and installing the implantable electronic device.

An example application for this system is an intraocular device containing electronics. Implanting an electronic intraocular device, such as an accommodating intraocular lens, may involve an incision of approximately 5 mm to install the hermetic electronics package in the first instance. However, the exemplary battery package is much smaller and can fit through a 1 mm incision for future battery replacements, which is the standard incision size for typical cataract surgery. Other implantable medical devices, such as pacemakers and cochlear implants, can also benefit from the system described herein.

It should be understood that the above embodiments, and other embodiments described herein, are provided for explanatory purposes, and are not intended to be limiting.

II. EXAMPLE SYSTEMS AND DEVICES

Figure 1:
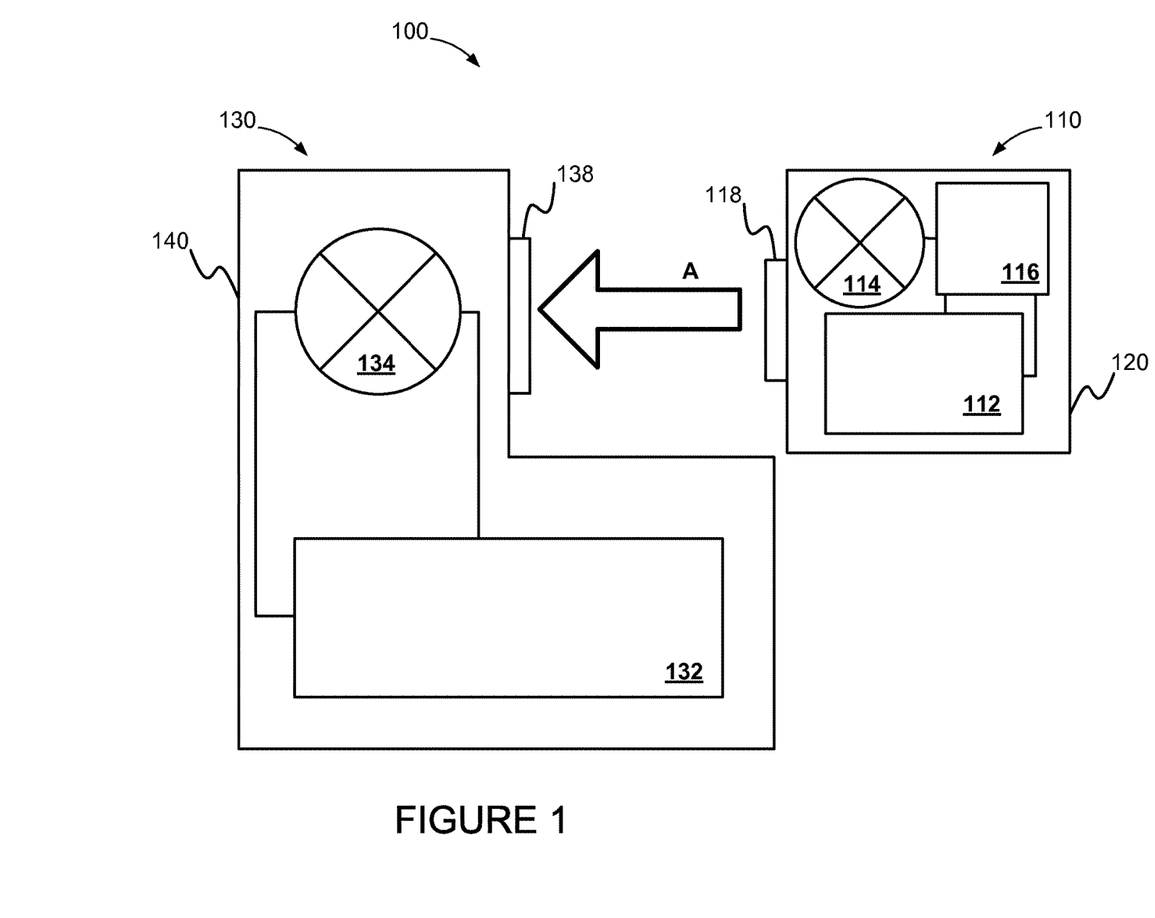
FIG. 1 is a block diagram of an example system that includes a battery package and an electronic device.

FIG. 1 is a block diagram of a system 100 that includes a battery package 110 in wireless communication with an electronic device 130. In some examples, the system 100, including battery package 110 and electronic device 130 may all be designed to be implanted in the body. Other applications are contemplated. The battery package 110 may include a battery 112, a wireless-power transceiver 114, and one or more alignment structures 118, configured to removably align the device with the electronic device 130. The one or more alignment structures 118 may be provided as any structure, device or mechanism capable of removably aligning the battery package 110 and the electronic device 130, such as magnets or snaps. Depending on the power consumption of the electronic device 130, as will be described further below, the battery 112 may be rechargeable or non-rechargeable. For example, where the electronic device 130 has high-power needs, the battery 112 of the battery package 110 may be a rechargeable battery.

At least the battery 112 and the wireless power transceiver 114 of the battery package 110 may be enclosed within a hermetic material 120. The hermetic material 120 may be any material for providing a water-tight and, in some cases an air-tight, seal such that the device 110 can be used in a wet environment. For example, the hermetic material 120 may be polytetrafluoroethylene (PTFE). The one or more alignment structures 118 can be placed within or outside of the hermetic material 120.

The electronic device 130 may include an electronics package 132 containing at least some of the electronic components that enable the features and functions of the electronic device 130. The electronic device 130 may also include a wireless transceiver 134 and one or more alignment structures 138 configured to removably align the electronic device 130 with the battery package 110. The one or more alignment structures 138 may correspond to or be complimentary to the one or more alignment structures 118 provided on the battery package 110. At least the electronics package 132 and wireless transceiver 134 of the electronic device 130 may be disposed within a hermetic material 140, such as described above with respect to hermetic material 120. The one or more alignment structures 138 may be within, or on the outside of the hermetic material 140.

Figure 2:
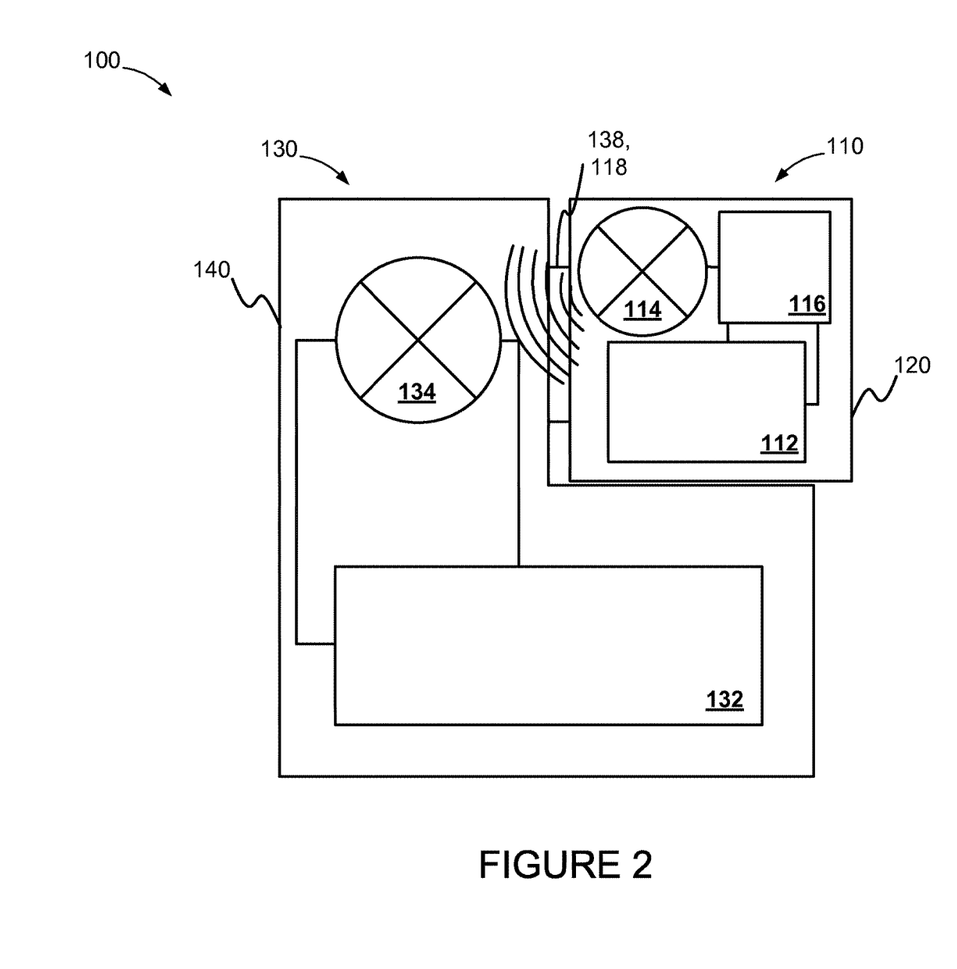
FIG. 2 is a block diagram of the example system illustrated in FIG. 1 in which the battery package is removably aligned with the electronic device.

As shown in FIG. 1, the battery package 110 and the electronic device 130 may be brought into alignment as indicated by arrow A. FIG. 2 is a block diagram of the system 100, illustrating the battery package 110 removably aligned with the electronic device 130 via the one or more alignment structures 118, 138. The shapes, orientations and configurations of the battery package 110 and the electronic device 130 illustrated in FIGS. 1 and 2 are merely schematic and exemplary and other orientations shapes, orientations and configurations of these elements, and the manner in which they are removably aligned are expressly contemplated. When the battery package 110 and the electronic device 130 are brought into alignment, they are not electrically connected. Accordingly, the electronic device 130 and the battery package 110 may not necessarily be in direct abutment with one another.

Figure 3:
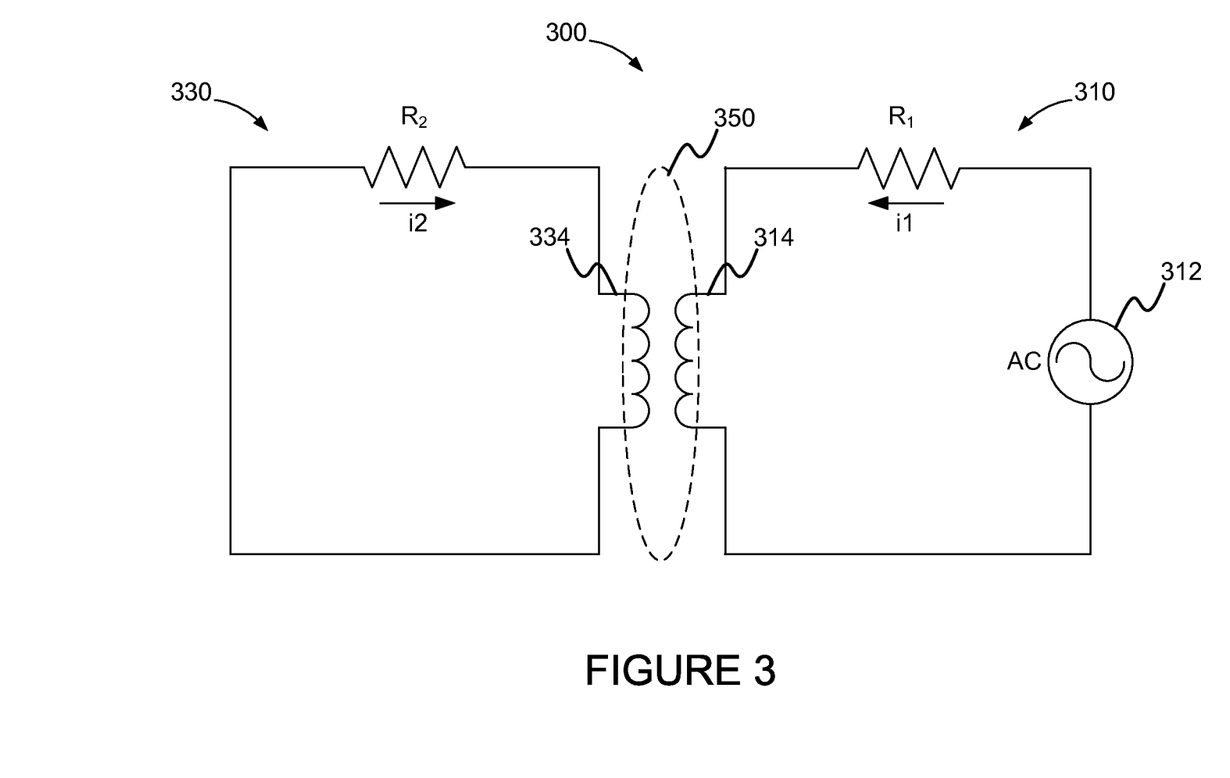
FIG. 3 is a block diagram of two inductively coupled electronic circuits.
Figure 4:
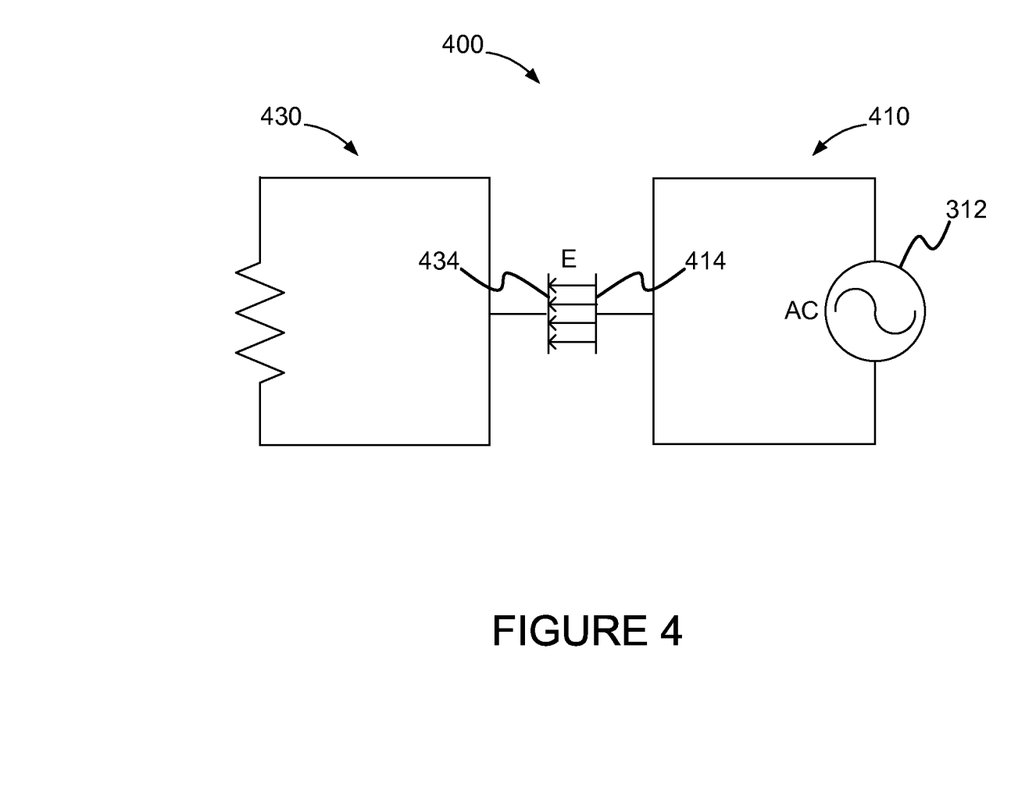
FIG. 4 is a block diagram of two capacitively coupled electronic circuits.

The wireless-power transceiver 114 of the battery package 110 is configured to wirelessly transfer power to the electronics package 134 of the electronic device 130. In one example, the wireless power transceiver 114 may be provided as an induction coil configured to wirelessly transfer power to the electronics package 134 by inductive coupling. FIG. 3 is a schematic illustration of an inductively coupled system 300, where the device 310 represents a battery package, such as battery package 110, and device 330 represents an electronic device, such as electronic device 130. The device 310 includes an AC power source 312, which can be powered by a battery, such as battery 112. Each of device 310 and device 330 include respective induction coils 314 and 334. When brought into proximity, power may be wirelessly transferred from the power source 312 of the device 310 to device 330 via induction coil 314 and 316 via inductive coupling. Generally, passing an alternating current i1 through the coil 114 generates a changing magnetic field 350. A current i2 is induced in the coil 334 when placed in close vicinity of the changing magnetic field 350 from the coil 314. The voltage and current induced in the coil 334 depend on the rate of current change through the coil 314. In another example, the wireless power transceiver 114 may be provided as an electrode, configured to wirelessly transfer power to the functional device electronics platform by capacitive coupling. FIG. 4 is a schematic illustration of a capacitive coupled system 400, where the device 410 represents a battery package, such as battery package 110, having an AC power source 412, and device 430 represents an electronic device, such as electronic device 130. Each of device 410 and device 430 include respective electrode plates 414 and 434. When brought into proximity, power may be wirelessly transferred from the power source 412 of the device 410 to device 430 via an electric field E generated between electrode plate 414 and electrode plate 434.

Because the battery package 110 and electronic device 130 are contained within separate hermetically-sealed packages and are not electrically or permanently physically connected, the battery package 110 may be easily separated from the installed or implanted electronic device 130 and replaced once the battery 112 expires. Expiration of the battery 112 may occur, for example, when it no longer recharges, will no longer hold a charge or otherwise does not function. Beneficially, the battery package 110 can be designed to be smaller in size than the overall size of the electronic device. For example, the battery package 110 may be approximately 1 mm long by 1 mm wide by 1 mm deep, whereas the electronic device may have larger dimensions, such as 5 mm. These features of the system 100 allow for replacement of the power source to the electronic device 130, i.e., the battery package 110, without having to remove and repair or replace the overall electronic device 130, which can have longer lifetime than that of a battery.

Many different electronic devices may benefit from the features of the system 100. In some examples, the electronic device 130 may be provided as an implantable electronic device, such as an intraocular implant, cochlear implant, or pacemaker. However, it is also contemplated that the electronic device 130 may be any electronic device requiring a power source, such as a battery. For example, the electronic device 130 may include any electronic device in which the power source may require replacement before the operational lifetime of the electronic device expires and in which extraction or replacement of the entire electronic device would be undesirable due to, for example, difficulty or expense. Further, the electronic device 130 may be any electronic device that is used in a wet environment, thereby requiring the electronic device to be hermetically-sealed. The features of the system 100 would allow for repair or replacement of the device's power source, without undesirably requiring the hermetic seal to be ruptured, as would be required if the electronic device were provided with an integral power source.

Returning to FIG. 1, in some cases, the battery package 110 may also include an electronic circuit 116 coupled to the battery 112 and the wireless power transceiver 114. The electronic circuit 116 may comprise an integrated circuit, such as an ASIC chip customized for this application, or it may comprise discrete electronic components. The electronic circuit 116 is configured to control the transfer of power from the battery 112, for example, by setting the frequency at which alternating current will be provided to the wireless transceiver 114 from the battery 112, or by operating as a switch between a power transmission and a non-power transmission mode.

Figure 5:
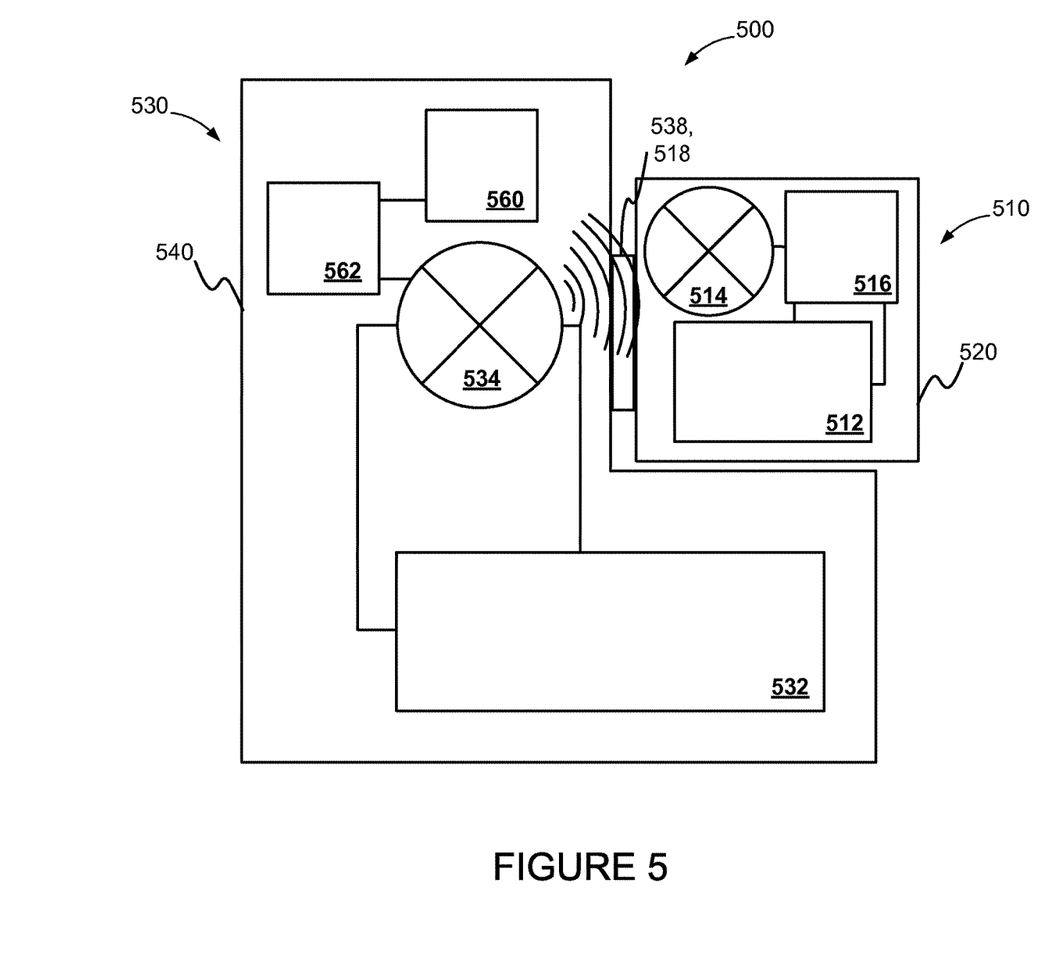
FIG. 5 is a block diagram of an example system that includes a battery package and an electronic device, in which the battery package is removably aligned with the electronic device.

FIG. 5 is a block diagram of a system 500 that includes a battery package 510 in wireless communication with an electronic device 530, brought into removable alignment via one or more alignment structures 518 on the battery package and one or more corresponding alignment structures 538 on the electronic device 530. The battery package 510 includes a battery 512 which, in this example, is a rechargeable battery, and a wireless transceiver 514, at least both of which may be enclosed in a hermetic material 520. In some examples, the battery package 510 may also include an electronic circuit 516 having similar functionality to that of electronic circuit 116. The electronic circuit 516, if provided, may also be enclosed within the hermetic material 520. The electronic device 530 is similar to electronic device 130, having an electronics package 532 and a wireless transceiver 534, separately enclosed within a hermetic material 540. In addition, the electronic device 530 includes an antenna 560 and an electronic circuit 562 coupled to the antenna 560 and the wireless transceiver 534. The antenna 560 may be an RF antenna configured to receive external RF signals. In operation, the battery 512 is recharged by wirelessly transferring power from the wireless transceiver 534 on the electronic device 530, as received from the antenna 560, to the wireless transceiver 514.

Electronic circuit 562, similar to electronic circuit 516, may be configured to control the receipt of wireless power via the antenna 560 and the transfer of wireless power from the wireless transceiver 534 to the wireless transceiver 514 on the battery package 510. In some examples, the electronic circuit 562 may be configured to receive a notification, in the form of a signal, from the electronic circuit 516 indicating the level of charge on the battery 512 or a notification of when the battery 512 needs to be recharged. The electronic circuit 562 may further be configured to control the antenna 560 in order to transmit the information received from the circuit 516 to a remote device, such as a smart phone or other computing device of a person monitoring or operating the electronic device 530, or of an individual within which the electronic device 530 is implanted.

III. EXAMPLE METHODS

Figure 6:
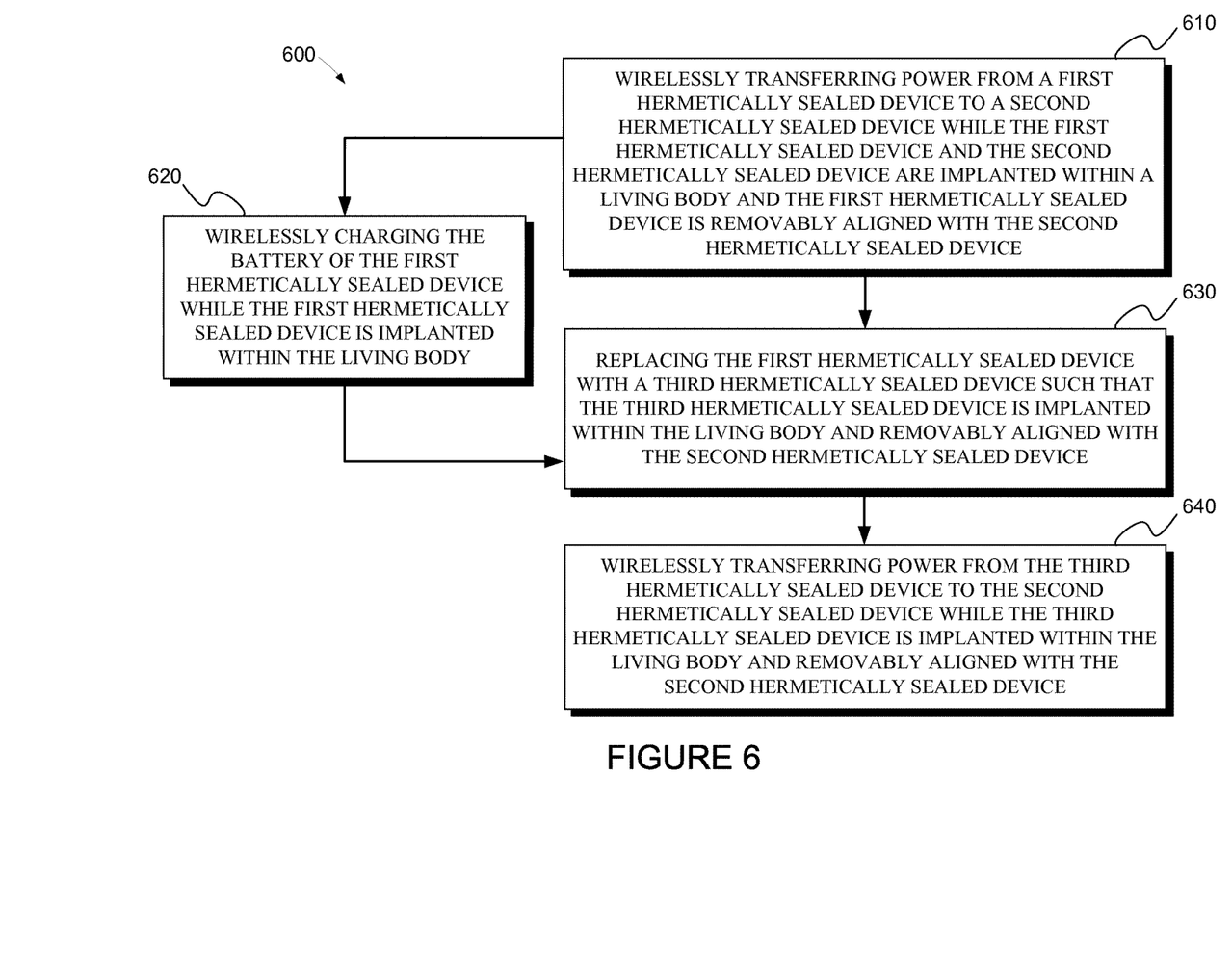
FIG. 6 is a flow chart of an example method, according to an example embodiment

FIG. 6 is a flowchart of an example method 600 for wirelessly transferring power between two hermetically sealed devices. The example methods described herein may be carried out by a system configured to wirelessly transfer power, such as systems 100 and 500. In a first step 610, power is wirelessly transferred from a first hermetically sealed device, such as a battery package 110, 510, to a second hermetically sealed device, such as electronic device 130, 530, while the first device is removably aligned with the second device. Power may be wirelessly transferred from the first hermetically sealed device to the second hermetically sealed device may any means of wireless power transfer, including inductive coupling and capacitive coupling. In some examples, both the first and second hermetically sealed devices are implanted within a living body. However, other applications in which hermetically-sealed electronic devices are used are contemplated herein. For example, the method may be carried out by two hermetically-sealed devices that are both submerged in a liquid environment. The first hermetically sealed device may include one or more alignment structures, configured to removably align the first hermetically sealed device with the second hermetically sealed device. In addition, the first hermetically-sealed device may include a battery and a wireless power transceiver. The second hermetically sealed device may also include a wireless power transceiver.

In some examples, the method 600 may further include a step 620 of wirelessly charging the battery of the first hermetically sealed device. This step 620 may be carried out while the first hermetically sealed device is implanted within a living body. In such examples, the second hermetically sealed device further includes an antenna and one or more electronic circuits coupled to the antenna and the wireless power transceiver. Wireless power, for example, in the form of an RF signal, may be received by the antenna. In response, the electronic circuit may cause the wireless power transceiver of the second hermetically-sealed device to wirelessly transfer power to the wireless power transceiver of the first hermetically-sealed device. Power received by the wireless power transceiver of the first hermetically-sealed device may be transmitted to the battery. By providing an antenna for receiving power from a remote source on the second hermetically-sealed device, the size of the first hermetically-sealed device may be limited, making it easier to remove and/or replace the first hermetically-sealed device if necessary. Step 620 may not be carried out in the method 600 if the battery of the first hermetically-sealed device is a non-rechargeable battery.

In some examples of method 600, the first hermetically sealed device may be replaced with a third hermetically sealed device and removably aligned with the second hermetically sealed device (630). The third hermetically sealed device may, in some cases, be implanted within the living body in this step. For example, when the battery of the first hermetically-sealed device expires, the first hermetically-sealed device, acting as a power source for the second hermetically-sealed device, may be replaced with a third hermetically-sealed device to act as a power source. Similar to the first hermetically-sealed device, the third hermetically sealed device may include one or more respective alignment structures configured to removably align the third hermetically sealed device with the second hermetically sealed device, a respective battery, and a respective wireless power transceiver. Power may be wirelessly transferred from the third hermetically sealed device to the second hermetically sealed device while, for example, the third hermetically sealed device is implanted within the living body and removably aligned with the second hermetically sealed device.

The second hermetically sealed device may be larger than the first and third hermetically sealed devices in at least one dimension. For example, as described above, battery package may be approximately 1 mm in length, whereas the electronic device is approximately 5 mm in length. Accordingly, when the devices are implanted in a living body, the first hermetically sealed device may be replaced with the third hermetically sealed device via an incision in the living body. As the first and third hermetically-sealed devices are smaller than the second device, the incision may be smaller than the second hermetically sealed device in the at least one dimension, such that the incision accommodates the first and third hermetically sealed devices but not the second hermetically sealed device.

IV. CONCLUSION

The present disclosure is not to be limited in terms of the particular embodiments described in this application, which are intended as illustrations of various aspects. Other embodiments can be utilized, and other changes can be made, without departing from the spirit or scope of the subject matter presented herein, as will be apparent to those skilled in the art. It will be readily understood that the aspects of the present disclosure, as generally described herein, and illustrated in the figures, can be arranged, substituted, combined, separated, and designed in a wide variety of different configurations, all of which are explicitly contemplated herein. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of example systems, devices, and methods with reference to the accompanying figures. In the figures, similar symbols typically identify similar components, unless context dictates otherwise. The example embodiments described herein and in the figures are not meant to be limiting. It should be understood that other embodiments can include more or less of each element shown in a given figure. Further, some of the illustrated elements can be combined or omitted. Yet further, an example embodiment can include elements that are not illustrated in the figures.

It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

What is claimed is:

1. A device, comprising:
    a battery and a wireless power transceiver, the wireless power transceiver configured to:
        wirelessly transfer power to an electronics package of a body-implantable electronic device; and
        wirelessly receive external radio-frequency signals from the body-implantable electronic device, wherein the external radio-frequency signals are received by an antenna of the body-implantable electronic device, and wherein both the battery and the wireless power transceiver are enclosed within a hermetic material; and
    one or more alignment structures enclosed within the hermetic material and configured to removably align the device with the electronics package of the body-implantable electronic device.

2. The device of claim 1, wherein the wireless power transceiver comprises an induction coil.

3. The device of claim 2, wherein the induction coil is configured to wirelessly transfer power to the electronics package by inductive coupling.

4. The device of claim 1, wherein the wireless power transceiver comprises an electrode.

5. The device of claim 4, wherein the electrode is configured to wirelessly transfer power to the electronics package by capacitive coupling.

6. The device of claim 1, further comprising one or more electronic circuits enclosed within the hermetic material and electrically coupled to the battery and the wireless power transceiver.

7. The device of claim 6, wherein the one or more electronic circuits comprise integrated circuits.

8. The device of claim 1, wherein the one or more alignment structures comprise magnets.

9. A body-implantable system, comprising:
    a hermetically sealed body-implantable electronic device comprising:
        an electronics package;
        a first wireless power transceiver; and
        an antenna that is distinct from the first wireless power transceiver; and
    a battery package, comprising:
        one or more alignment structures, configured to removably align the battery package with the body-implantable electronic device;
        a battery; and
        a second wireless power transceiver,
    wherein at least the battery and the second wireless power transceiver are contained within a hermetic material separate from the body-implantable electronic device, wherein the antenna is configured to receive external radio-frequency signals, and wherein the first wireless power transceiver and the second wireless power transceiver are configured to;
- wirelessly transfer power from the battery to the electronics package; and
- wirelessly transfer the external radio-frequency signals from the antenna to the battery.

10. The system of claim 9, wherein the second wireless power transceiver comprises an induction coil.

11. The system of claim 10, wherein the induction coil is configured to wirelessly transfer power to the electronics package by inductive coupling.

12. The system of claim 9, wherein the second wireless power transceiver comprises an electrode.

13. The system of claim 12, wherein the electrode is configured to wirelessly transfer power to the electronics package by capacitive coupling.

14. The system of claim 9, wherein the battery package further comprises one or more electronic circuits enclosed within the hermetic material and electrically coupled to the battery and the second wireless power transceiver.

15. The system of claim 9, wherein the external radio-frequency signals charge the battery.

* * * * *